US008686364B1

United States Patent
Little, III et al.

(10) Patent No.: US 8,686,364 B1
(45) Date of Patent: Apr. 1, 2014

(54) METHOD AND SYSTEM FOR DETERMINING ENERGY CONTENT AND DETECTING CONTAMINANTS IN A FLUID STREAM

(71) Applicant: JP3 Measurement, LLC, Austin, TX (US)

(72) Inventors: Joseph Paul Little, III, Austin, TX (US); Matthew R. Thomas, Austin, TX (US)

(73) Assignee: JP3 Measurement, LLC, Austin, TX (US)

( * ) Notice: Subject to any disclaimer, the term of this patent is extended or adjusted under 35 U.S.C. 154(b) by 0 days.

(21) Appl. No.: 13/720,598

(22) Filed: Dec. 19, 2012

Related U.S. Application Data (60) Provisional application No. 61/702,151, filed on Sep. 17, 2012.

(51) Int. Cl.
| | |
|---|---|
| G01J 5/02 | (2006.01) |
| G01N 21/35 | (2006.01) |
| G01N 21/39 | (2006.01) |
| G01N 21/17 | (2006.01) |
| G01J 3/433 | (2006.01) |
| G01J 3/10 | (2006.01) |

(52) U.S. Cl.
CPC .............. *G01N 21/359* (2013.01); *G01N 21/39* (2013.01); *G01N 2021/1736* (2013.01); *G01J 3/4338* (2013.01); *G01J 3/108* (2013.01)
USPC .................................................. 250/339.12

(58) Field of Classification Search
CPC ...... G01J 3/108; G01J 3/4338; G01N 21/359; G01N 21/39; G01N 2021/1736
USPC .................................................. 250/339.12
See application file for complete search history.

(56) References Cited

U.S. PATENT DOCUMENTS

| | | | |
|---|---|---|---|
| 4,818,348 A | * | 4/1989 | Stetter ........................... 205/780 |
| 5,528,036 A | | 6/1996 | Achter et al. |

(Continued)

FOREIGN PATENT DOCUMENTS

| | | |
|---|---|---|
| EP | 1 508 794 | 2/2005 |
| WO | WO 2007/143474 | 12/2007 |
| WO | WO 2012/050669 | 4/2012 |

OTHER PUBLICATIONS

Weldon et al., "H2S and CO2 gas sensing using DFB laser diodes emitting at 1.57 um", Sensors and Actuators B 29, 1995, pp. 101-107.*

(Continued)

*Primary Examiner* — David Porta
*Assistant Examiner* — Mindy Vu
(74) *Attorney, Agent, or Firm* — DuBois, Bryant & Campbell, LLP; William D. Wiese (57) ABSTRACT

Methods and systems for real time, in situ monitoring of fluids, and particularly the determination of both the energy content and contaminants in a gas or oil transmission facility, are provided. The system may include two separate scanning sources to scan two different, but overlapping, NIR ranges, or may involve two separate scans from a single scanning spectroscopy source. The first scan ranges from approximately 1550 nm up through 1800 nm and a second scan concurrently scans at a high resolution across a band from approximately 1560-1610 nm, the wavelength of interest for hydrogen sulfide (though similar scans are contemplated in alternative wavelength ranges for alternative contaminants). The second scan may provide very narrow (0.005 nm) step resolution over just the wavelength of interest for the contaminant and may scan at a substantially higher power level. The spectroscopic optical data from the two scans, however obtained, must then be combined into an analytical processing module containing models that analyze the multi-scan data and yield both energy content and contaminant quantitative data.

30 Claims, 5 Drawing Sheets

(56) References Cited

U.S. PATENT DOCUMENTS

| | | | |
|---|---|---|---|
| 5,822,058 A * | 10/1998 | Adler-Golden et al. | 356/303 |
| 6,292,756 B1 | 9/2001 | Lievois et al. | |
| 6,939,717 B2 * | 9/2005 | Jiang et al. | 436/121 |
| 2006/0211129 A1 | 9/2006 | Stevens et al. | |
| 2007/0045543 A1 * | 3/2007 | May | 250/339.13 |
| 2008/0087078 A1 * | 4/2008 | Vannuffelen et al. | 73/152.54 |
| 2008/0156088 A1 * | 7/2008 | Hsu et al. | 73/152.23 |
| 2008/0225289 A1 | 9/2008 | Gould et al. | |
| 2010/0090845 A1 | 4/2010 | Polak et al. | |
| 2010/0228688 A1 * | 9/2010 | Little et al. | 705/413 |
| 2010/0277727 A1 | 11/2010 | Schlaminger | |
| 2011/0019193 A1 * | 1/2011 | Danno et al. | 356/433 |
| 2012/0064635 A1 * | 3/2012 | Feitisch et al. | 436/133 |

OTHER PUBLICATIONS

International Search Report and Written Opinion issued Jan. 29, 2014 in corresponding International Application No. PCT/US13/60087.

* cited by examiner

METHOD AND SYSTEM FOR DETERMINING ENERGY CONTENT AND DETECTING CONTAMINANTS IN A FLUID STREAM

PRIORITY STATEMENT

Under 35 U.S.C. §119 & 37 C.F.R. §1.78

This non-provisional application claims priority based upon prior U.S. Provisional Patent Application Ser. No. 61/702,151 filed Sep. 17, 2012 in the names of Joseph Paul Little, III and Matt Thomas entitled "Trace $H_2S$ Detection with Near IR Spectroscopy in Natural Gas Stream Under Pressure Utilizing a Scanning Light Source," the disclosure of which is incorporated herein in its entirety by reference as if fully set forth herein.

BACKGROUND OF THE INVENTION

This invention relates to the real time, in situ monitoring of fluids, and especially to the determination of contaminants in a fluid infrastructure. The invention is directed in particular to the detection of hydrogen sulfide in a natural gas transmission line, but aspects of the invention may be employed to detect other contaminants in other environments as well.

Natural gas is a mixture primarily of methane ($CH_4$) and other hydrocarbons plus carbon dioxide ($CO_2$), nitrogen ($N_2$), hydrogen sulfide ($H_2S$) and water ($H_2O$). The hydrogen sulfide component is an extremely toxic and irritating gas, causing eye irritation, dizziness, coughing, and headaches at low concentrations and unconsciousness or death at higher concentration if released into the local environment. In addition to its adverse human health effects, the presence of hydrogen sulfide in natural gas can cause sulfide stress cracking and hydrogen-induced cracking to the lines through which the gas is transmitted. Consequently, most natural gas processing facilities treat natural gas to neutralize the hydrogen sulfide, so it is important to accurately measure the amount of hydrogen sulfide present so that appropriate amounts of chemical neutralizer may be added. For these and other reasons, it is important to be able to accurately detect the amount of hydrogen sulfide in the system during transmission.

Near infrared (NIR) spectrographic analysis is the preferred method for determining the composition of natural gas because, unlike with gas chromatography, there is no need for calibration gases, carrier gases or filters to perform measurements. The measurements are made at the operating temperature and pressure of the fluid infrastructure without the need to extract and alter a representative sample, thereby minimizing the possibility of sample contamination and the risk of analyzing material that is not truly representative of the fluid in the process line. Also, the presence of liquid condensate in the gas stream cannot be measured by a gas chromatography system, but can be detected by an NIR spectrometer.

Near-infrared spectroscopy generally operates in the 1350 to 2500 nanometer (nm), or 1.35 to 2.5 micrometer (μm), wavelength region. The strongest absorption frequencies of most hydrocarbon gases fall between 1600 and 1800 nm, while the NIR absorption spectra of hydrogen sulfide falls between approximately 1570 and 1610 nm. Though this absorption band for hydrogen sulfide is relatively weak, it nevertheless means that NIR spectroscopy is an excellent candidate for both determining the energy content of the natural gas and determining the degree to which hydrogen sulfide is present.

Unfortunately, determining the amount of hydrogen sulfide in situ in a natural gas stream under pressure is extremely difficult. Hydrogen sulfide is a very weak NIR absorber and, as a result, the signal-to-noise ratio is very low. This is complicated by the fact that there are species of hydrocarbons in natural gas whose absorption frequencies may interfere with hydrogen sulfide's absorption frequency, most notably methane ($CH_4$) and carbon monoxide (CO), but in some cases also some of the larger alkane molecules such as propane ($C_3H_8$). Finally, because absorption lines broaden with increasing pressure and temperature, hydrogen sulfide analysis with tunable diode lasers that are only capable of creating a very narrow range of NIR excitation frequency and focus on a single absorption peak is restricted to a certain maximum pressure and process temperature.

There is a need, therefore, for a method and system for using NIR spectroscopy in situ, under operating pressure, and in real time to reliably detect both the energy content of a fluid as well as the presence of trace quantities of hydrogen sulfide in the fluid. This system must be able to detect multiple absorbance bands of the hydrogen sulfide molecule over the high resolution scan and be able to distinguish these from the other peaks in the region.

SUMMARY

In one embodiment, two separate scanning sources scan two different, but overlapping, NIR ranges. The first scanning source scans from approximately 1550 nm up through 1800 nm and a second scanning source, such as a tunable diode laser, concurrently is made to scan at a much higher resolution across a band from approximately 1560-1610 nm, the wavelength of interest for hydrogen sulfide. The second scanning source may provide, for example, a very narrow (e.g. 0.005 nm) step which results in a very high resolution over just the wavelength of interest for hydrogen sulfide and may scan at a substantially higher power level.

In another embodiment of the present invention, a single scanning source conducts two separate scans in sequence, the results of which are then combined to determine both energy and contaminant content of the stream. The scanning source may first be set to scan the range from approximately 1350 to 1800 nm at a lower resolution to determine energy content and other contaminant content (for example, water or $CO_2$). The same scanning source will then be set in high-resolution scanning mode to scan the hydrogen sulfide region of interest at a higher resolution and power, often repeating many scans over this same region for every one scan over the full 1350-1800 nm region.

In another embodiment, the first scanning source again scans from below approximately 1550 nm up through 1800 nm at a lower resolution. However, rather than employing a second scanning source, software is used to increase the resolution of the range between 1560 and 1610 nm, the hydrogen sulfide range, so as to distinguish the hydrogen sulfide peaks from the noise and contributions from other species present in the fluid stream.

In each of the foregoing cases, post-processing methods can be utilized to standardize the results, such as calculating the first derivative, normalizing for pressure, and possibly using other processing techniques, such as extended multiplicative scatter correction. In addition, post-processing methods can be used to calculate or otherwise determine the amount of each constituent of interest in the gas stream based on the combined spectroscopic data obtained with the multiple, varied scans.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The present invention is directed to improved methods and systems for, among other things, detecting contaminants in a fluid stream. The configuration and use of the presently preferred embodiments are discussed in detail below. It should be appreciated, however, that the present invention provides many applicable inventive concepts that can be embodied in a wide variety of contexts other than determination of energy content and detection of contaminants in a fluid stream. Accordingly, the specific embodiments discussed are merely illustrative of specific ways to make and use the invention, and do not limit the scope of the invention. In addition, the following terms shall have the associated meaning when used herein:

"fluid infrastructure" means any infrastructure used in connection with the collection, processing, storage, transmission or distribution of a fluid including, without limitation, if the fluid is a hydrocarbon, any infrastructure between the wellhead and the point of retail delivery;

"contaminant" means any undesirable or less desirable chemical within a fluid;

"fluid" means any gas or liquid, including but not limited to a natural gas stream with or without suspended liquids;

"high resolution" means NIR scans with resolution greater than or equal to 0.01 nanometers;

"high-resolution scanning mode" means scanning at a high resolution over a narrow range of wavelengths;

"low resolution" means NIR scans with resolution in the 0.5 nanometer to 5 nanometer range;

"NIR" and "near infrared" mean the wavelength range between approximately 1350 to 2500 nanometer, or 1.35 to 2.5 micrometer;

"scanning source" means any light source known in the art for scanning the near infrared spectrum, including common incandescent bulbs, quartz halogen bulbs, light-emitting diodes, and tunable diode lasers; and "TDL" means a tunable diode laser, typically used with very narrow beam width at a single set wavelength corresponding to highest absorption of a molecule of interest in a spectroscopic system.

Embodiments of the present invention provide a spectrometer, an optical system and a processing module to determine both the quantity of energy (such as that determined by the hydrocarbon speciation and percentages) and the amount of one or more contaminants in a fluid stream, typically in a fluid infrastructure. In some cases, these contaminants are weak absorbers so their signal is lost or impaired by the noise in the spectrographic system. In other cases, the absorption signal of the contaminant is convoluted with other absorption signals making a precise determination of the chemical of interest seemingly inaccurate or impossible. Through use of the embodiments of the present invention, it is possible to determine the energy content of the fluid as well as the quantity of the contaminants of interest in the fluid.

Figure 1:
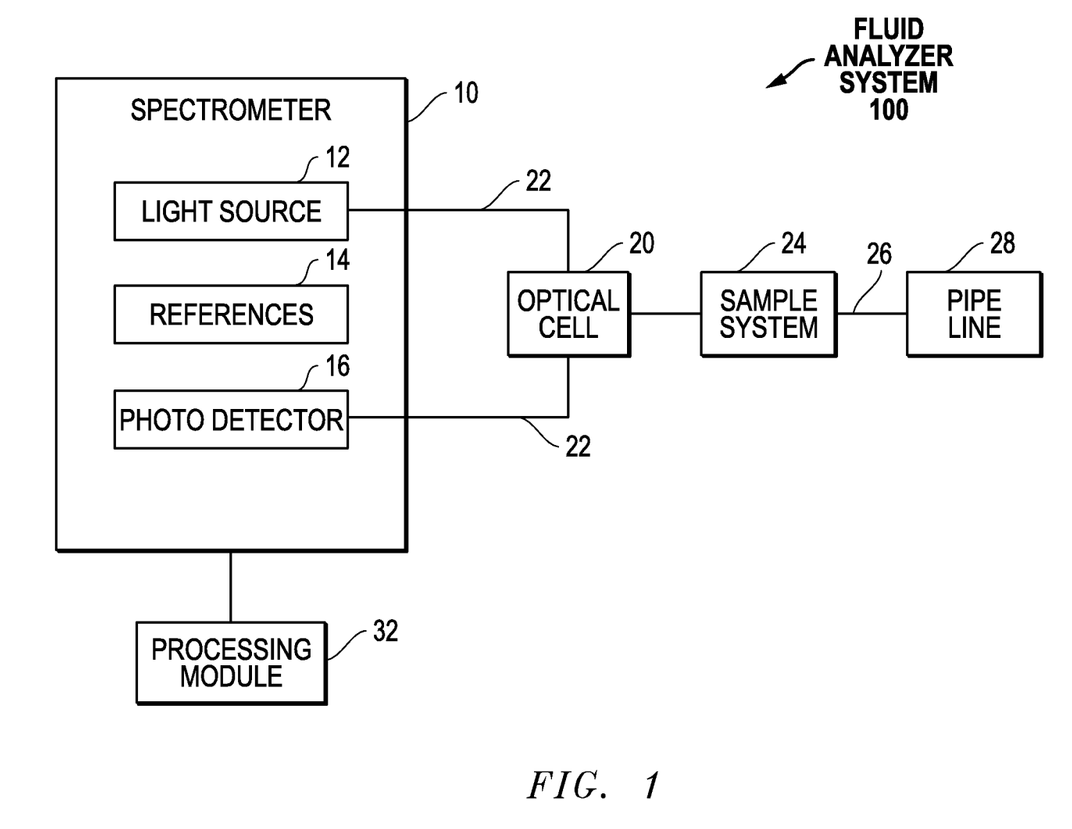
FIG. 1 provides a block diagram of a spectrometer operable to perform spectrographic analysis of fluids in the field.

A representative embodiment of a fluid analyzer system 100 is shown in FIG. 1. A spectrometer 10 known in the art includes a light source 12, integrated wavelength and amplitude references 14, and a photo detector 16. Spectrometer 10 is coupled to an optical cell 20 via fiber optic cables 22. A sample system 24 will extract gas 26 from a pipe line 28, whether in situ or as a bypass configuration, measure the pressure and temperature of the gas, direct the gas through optical cell 20 where it will be exposed to light from the scanning source 12, and reintroduce the sample back into the transmission line 28 or exhaust it to atmosphere. The spectral data will be transmitted back to the photo detector 16 via the fiber optic cables 22. The detector array may, for example, be an Indium Gallium Arsenide (InGaAs) photo detector. The processing module 32 will process the spectrographic data and other measured fluid properties such as temperature and pressure, using various models and computational techniques to determine the chemical composition of the gas. Other properties of the gas such as hydrocarbon dew point, specific gravity and compressibility, may also be computed from the information collected. The results will then be stored for a later transmission and analysis, sent directly to a data gathering location, or both.

The processing module 32 may be a single processing device or a plurality of processing devices. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The processing module 32 executes operational instructions corresponding to at least some of the steps and/or functions illustrated in FIG. 2.

Figure 2:
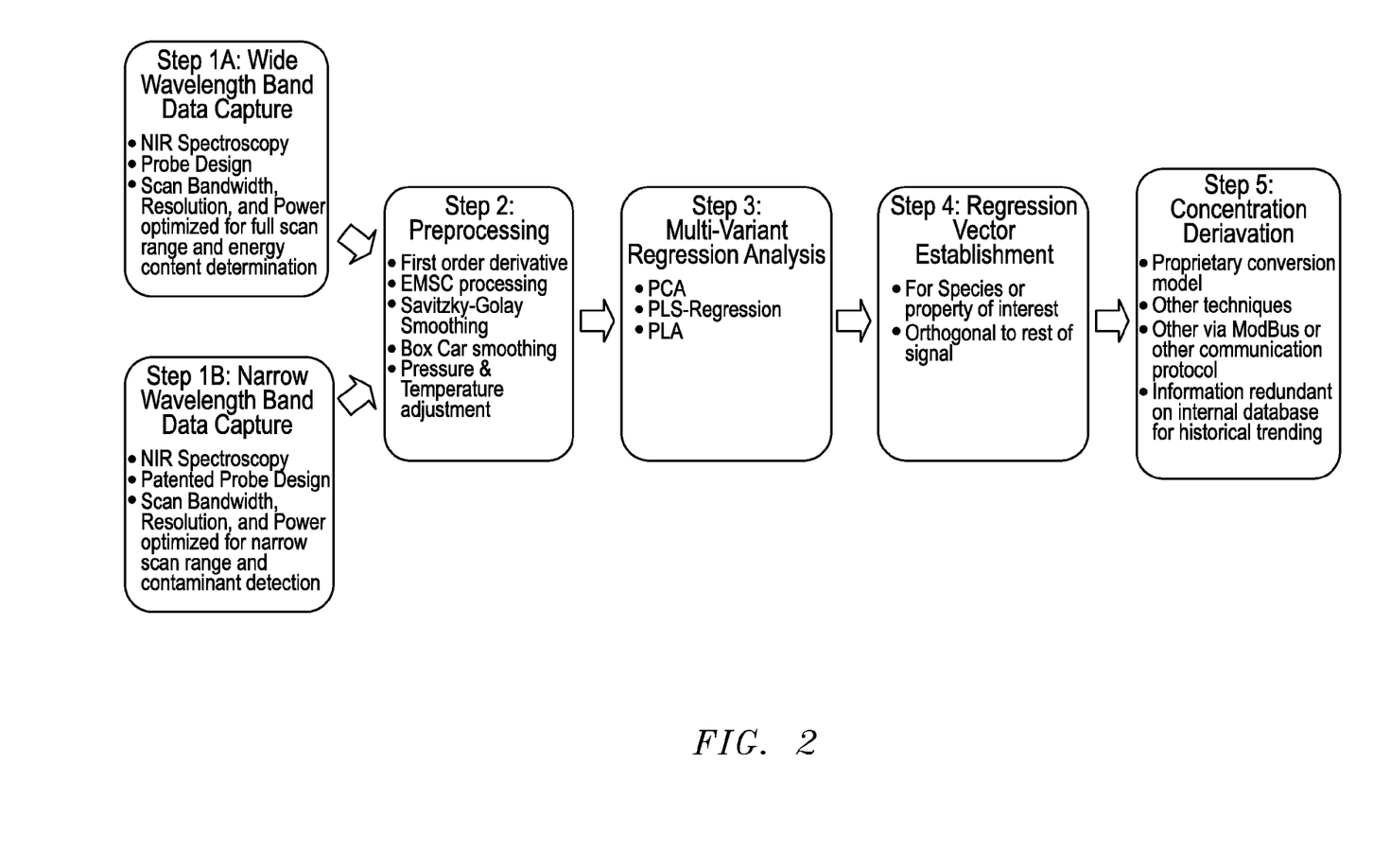
FIG. 2 provides a process flow diagram.

FIG. 2 provides a process flow diagram for a method to optically determine the amount of a contaminant and the energy content in a fluid using, for example, fluid analyzer system 100. In Step 1, the raw data is collected using a NIR spectroscopy system and an optical cell in a fluid transportation system. In Step 1A, the NIR spectroscopy system is made to scan across the wide wavelength band, with its scan parameters such as wavelength resolution and power set to optimize detection of those constituents that determine energy content. In Step 1B, which in this embodiment is indicated to happen sequentially after Step 1A but in other embodiments occurs simultaneously with Step 1A, the NIR spectroscopy system is made to scan across the narrow wavelength band, with its scan parameters such as wavelength resolution and power set to optimize detection of contaminants such as hydrogen sulfide. This raw data collected from Steps 1A and 1B is then sent to Step 2, Preprocessing, where the data is processed and manipulated using certain models and algorithms such as taking the first order derivative, EMSC processing, Savitzky-Golay smoothing, box car smoothing, and/or pressure & temperature adjustment. This preprocessed data is then sent to Step 3, wherein a multivariate regression analysis is performed on the data, followed by the regression vector establishment in Step 4. All of this processed data is then provided to the proprietary concentration derivation models in Step 5, yielding the desired output values for both contaminant concentration and energy content in the fluid stream of interest.

Generally speaking, there may not be enough resolution in the wide wavelength band to determine the amount of contaminate and the narrow wavelength band is likely too narrow to determine the full energy content of the fluid. Therefore, in many embodiments the two measurements are independent measurements. However, it is possible to include "markers" in the broad scan to help identify the presence of a contaminate. In some embodiments, the scan of the wide wavelength band can be used as a diagnostic tool to validate the results of the scan of the narrow wavelength band. For example, the results of the broad wavelength scan may be used as a rough method of determining whether concentrations of a contaminant are present above a certain threshold (e.g. a hydrogen sulfide concentration above 20 ppm).

Figure 3:
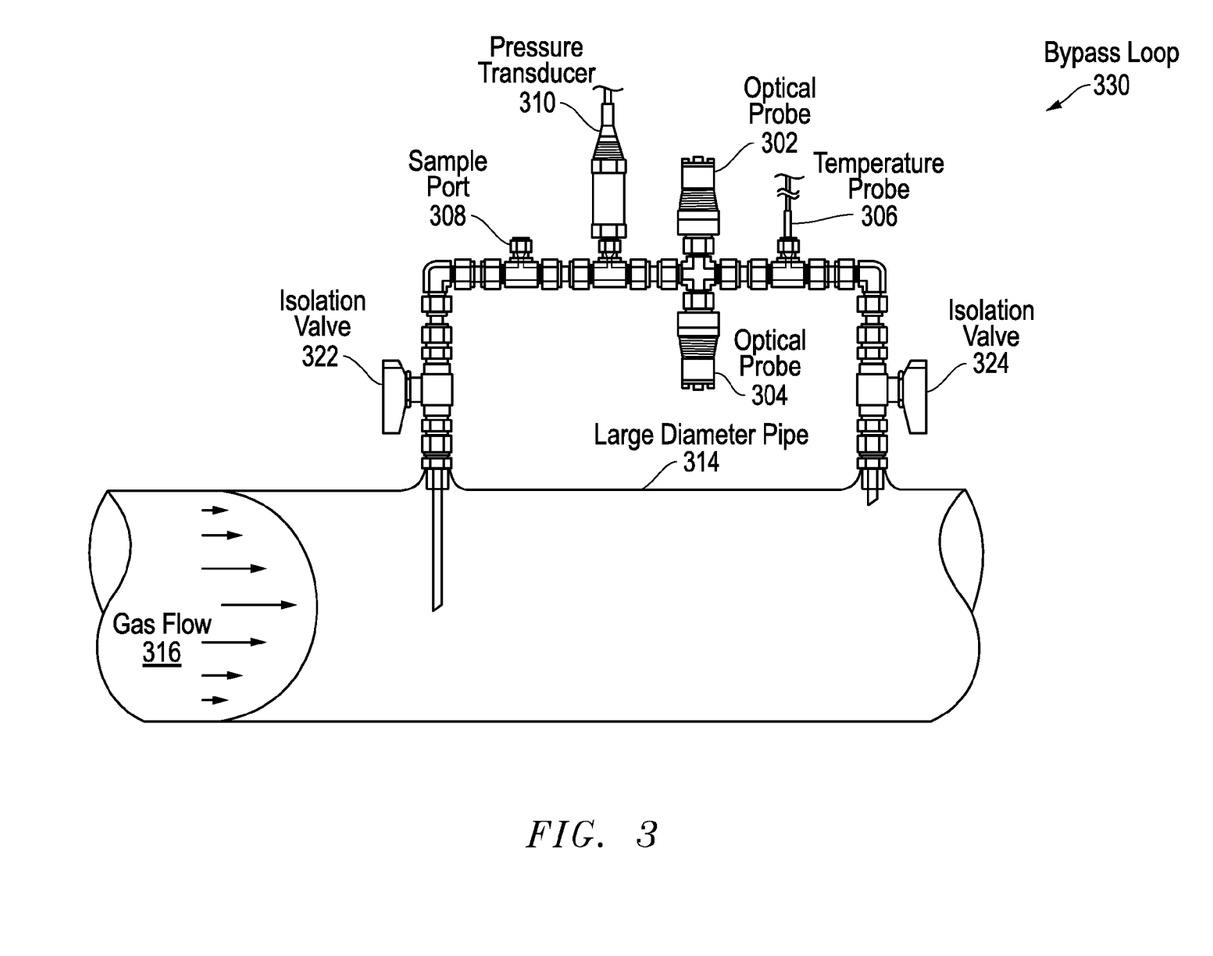
FIG. 3 depicts a system operable to measure the chemical composition of a gas within a pipeline.

FIG. 3 depicts an application of the foregoing methodology in a natural gas measurement system in which individual probes are introduced to a large diameter pipe 314 to measure the chemical composition of a gas 316 within a pipeline using a bypass loop 330. As depicted here, the sample system 24, optical cell 20, and pipeline 28 of fluid analyzer system 100 would be encompassed in a bypass loop 330. This loop would include isolation valves 322 and 324, optical probes 302 and 304, temperature probe 306, a sample port 308, and a pressure transducer 310. Optical probes 302 and 304 allow spectroscopic measurements to be taken and combined with the results of the pressure transducer 310 and temperature transducer 306 in order to yield information about the quantity of contaminants within the transmission pipe in which the analyzer 100 is installed.

While it is possible to measure many contaminants using the methodology described above, it is extremely difficult to determine the quantity of hydrogen sulfide in situ in a natural gas stream under pressure. First, as described above, hydrogen sulfide is a very weak absorber in the NIR and the signal-to-noise ratio is very low. As a result, the absorption lines for hydrogen sulfide provide a very weak signal. In addition, these hydrogen sulfide bands may become convoluted with absorption lines from other components of the gas, such as methane and heavier alkanes such as propane. Representative infrared absorption lines for various gases are given in Table 1. It should be kept in mind that, when reading a given line, consideration must be paid the fundamental line strength as well as to whether the line might overlap with the absorption lines of other gases that might be present in the sample.

TABLE 1

| Gas | Formula | Peak Absorption Wavelength (nm) |
|---|---|---|
| Water | H2O | 1392 |
| Ammonia | NH3 | 1512 |
| Carbon Monoxide | CO | 1560 |
| Carbon Monoxide | CO | 1579 |

TABLE 1-continued

| Gas | Formula | Peak Absorption Wavelength (nm) |
|---|---|---|
| Hydrogen Sulfide | H2S | 1579 |
| Methane | CH4 | 1654 |
| Methane | CH4 | 1684 |
| Hydrochloric Acid | HCl | 1730 |
| Nitric Oxide | NO | 1790 |
| Water | H2O | 1800 |
| Water | H2O | 1854 |
| Water | H2O | 1877 |
| Water | H2O | 1826 |
| Nitrous Oxide | N2O | 1960 |
| Carbon Dioxide | CO2 | 2003 |
| Carbon Dioxide | CO2 | 2012 |
| Water | H2O | 2750 |

Finally, because absorption lines broaden with increasing temperature and pressure, hydrogen sulfide analysis with tunable diode lasers is typically restricted to a maximum pressure and process temperature of approximately 2 bar absolute and 300° C. The absolute signal for hydrogen sulfide at the same volume ratio at different pressures will be different due to pressure "broadening." Broadening is the widening of the absorption band of a given molecule ($H_2S$ in this case) due to the increased interaction and changes in collision frequency between the molecules as the pressure increases. Temperature also has a broadening effect but the magnitude is much less than pressure. Variance in the composition of the sample gas will also change the absolute signal due to the interactions between the component gas molecules. Thus the absolute signal is a function of the state of the gas. This invention, in part, contemplates techniques that can be employed to overcome these challenges and correlate the absolute signal obtained from NIR spectroscopy to a direct correlation of the concentration of hydrogen sulfide while also determining the energy content of the fluid stream.

In one embodiment of the present invention, two separate scanning sources are employed and combined with certain data processing techniques and models to provide a real time, in situ measurement of both the energy content of the fluid and the amount of a contaminant in the fluid. The first scanning source scans from a frequency at or lower than the range of interest (i.e. below approximately 1550 nm) up through 1800 nm at a low resolution. A second scanning source, such as a tunable diode laser, concurrently or nearly simultaneously scans at a high resolution across only the narrow wavelength of interest for a contaminant, such as hydrogen sulfide for which the wavelength of interest is approximately 1560-1610 nm. For example, the second scanning source may provide very narrow (e.g. 0.005 nm) step which enables very high resolution over just the wavelength of interest for hydrogen sulfide and may scan at the highest power level possible. The signals obtained from the combined low resolution scan and high resolution scan are used to calculate the chemical composition of the fluid and the amount of hydrogen sulfide or other contaminant in the fluid.

Figure 4:
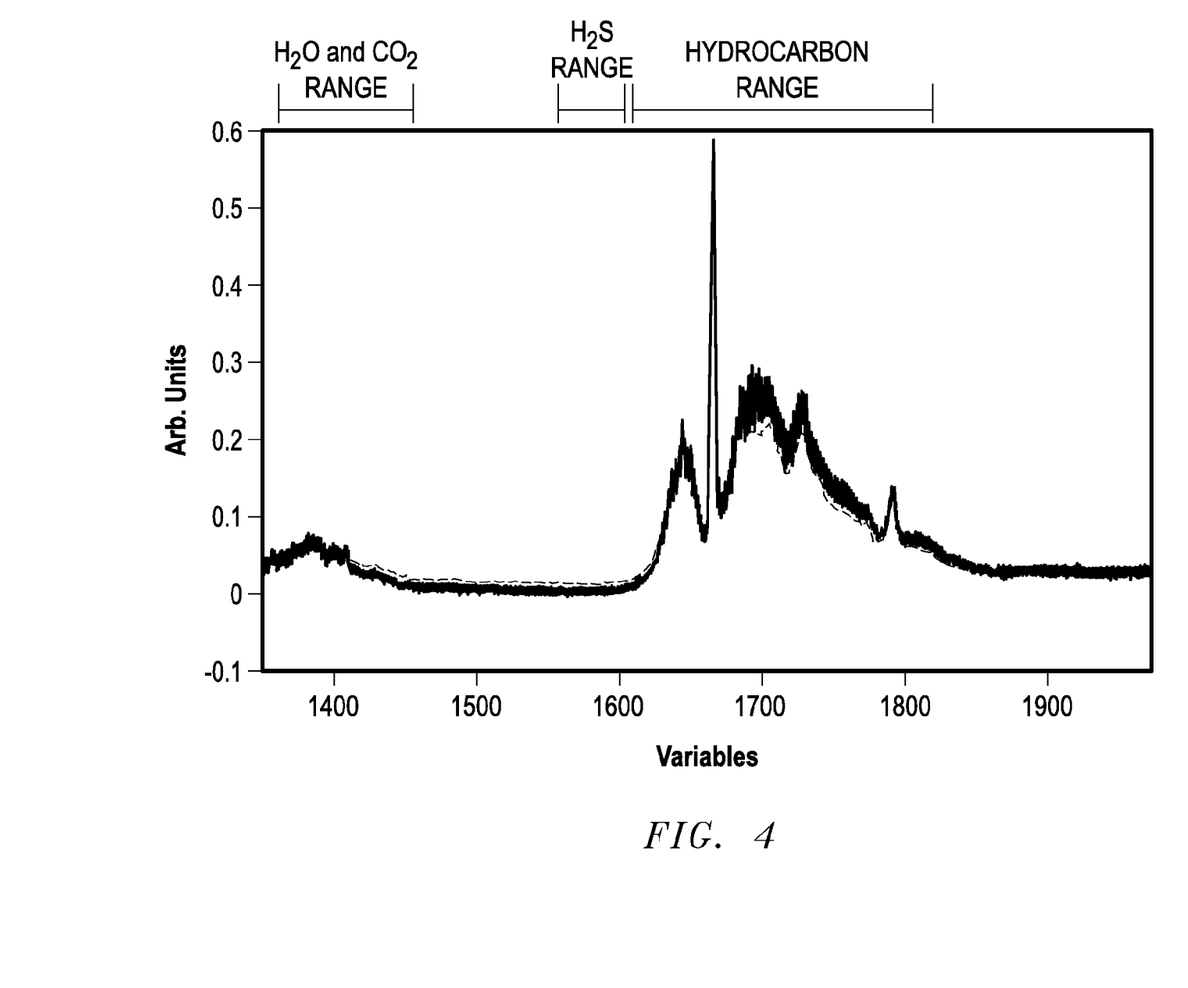
FIG. 4 shows an example of a collected absorption spectra showing absorption versus wavelength between 1350 and 1800 nm.
Figure 5:
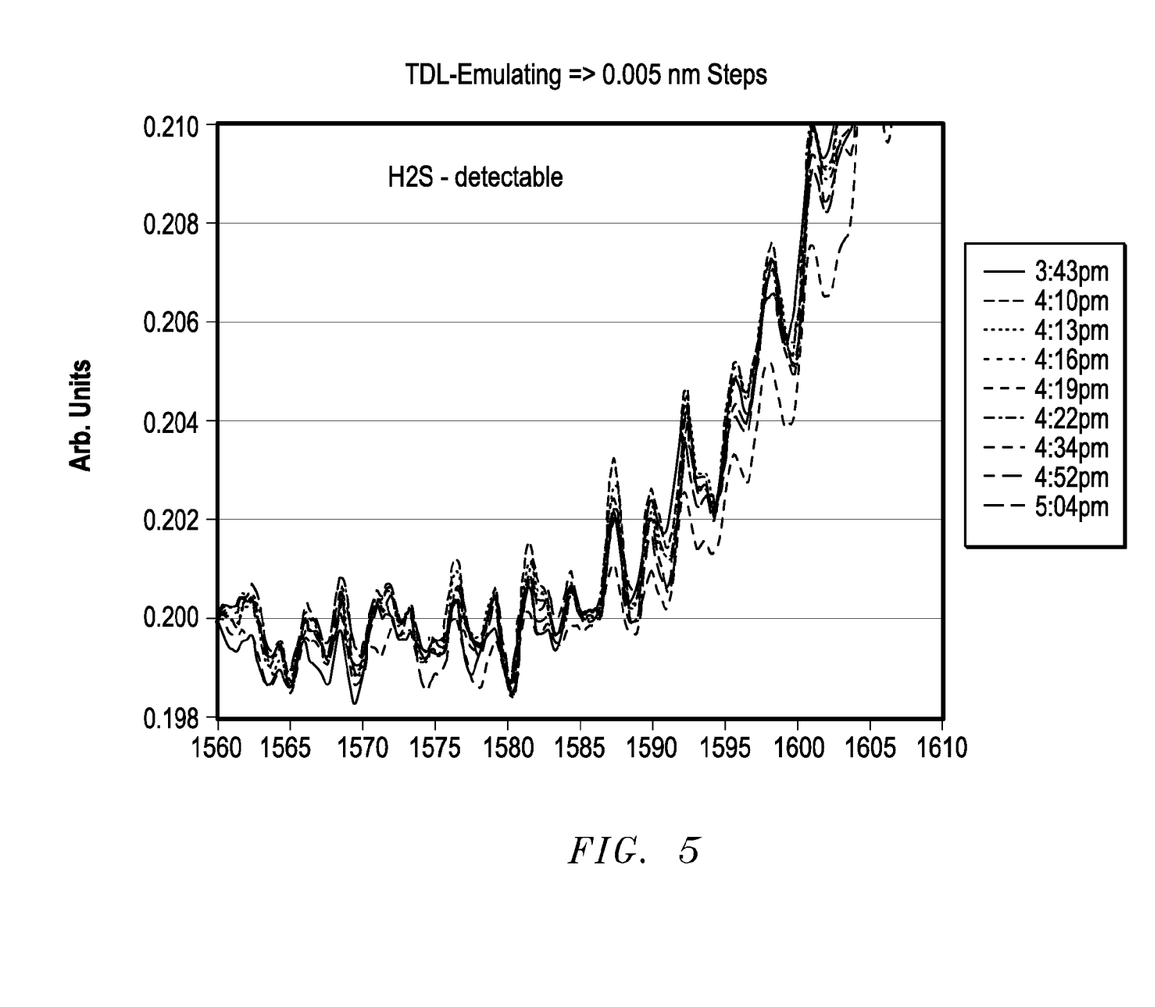
FIG. 5 shows an example of a collected spectrum using one embodiment of the present invention plotting absorption against wavelengths between 1560 nm and 1610 nm.

As one example of the embodiment described above, FIG. 4 shows an absorption spectra between 1350 and 1975 nm resulting from the first scanning source scanning a broad range at low resolution as described above. It is evident that the hydrocarbon range between 1600 and 1800 nm is active, but there is no discernible information in the hydrogen sulfide wavelength range between 1560 and 1610 nm. The hydrogen sulfide wavelength range may be scanned using a second scanning source at a higher resolution, in this case 0.005 nm steps, and the result is shown in FIG. 5. As can be seen in FIG. 5, the smooth appearance of the absorption curve in the hydrogen sulfide range in FIG. 4 is actually a series of peaks and valleys that is not detectable at the lower resolution of the first scanning source.

In another embodiment of the present invention, one scanning source conducts two separate scans. The scanning source will first be set to perform a broad scan (e.g. from 1350 to 1800 nm) at a low resolution to determine energy content, and the same scanning source will then scan in high-resolution scanning mode to scan at a high resolution through the hydrogen sulfide wavelength region of interest. The signals from each scan will be processed through the same above-mentioned processing steps, or alternatively, the extended multiplicative scatter correction and/or other preprocessing steps could be eliminated from the second scan. The processing module 32 could combine the optical data obtained from the multiple scans (high-bandwidth low-resolution and low-bandwidth high-resolution) to calculate both the energy content and the contaminant quantity simultaneously.

Some tunable diode lasers (TDLs) known in the art have a very narrow wavelength range, and thus a very high resolution. The prior art takes advantage of this by only focusing on a single peak of hydrogen sulfide absorption; however, there are two problems with this approach in actual gas streams. The first is that other species of gas (for example, methane) that may be present in the gas stream will have overlapping absorption spectra with the hydrogen sulfide, and if only the narrow spectra is considered then the methane cannot be distinguished from the hydrogen sulfide. Additionally, if the pressure is increased, the hydrogen sulfide absorption peak gets broadened and the ability to achieve accurate measurement using just a very narrow, non-scanned beam such as that of a TDL is compromised. Embodiments of the present invention employ a very high resolution source that scans the responsive range of the hydrogen sulfide signal in the NIR and thus overcomes both of these obstacles.

In embodiments of the current invention, the second scanning source scans across a specific, narrower range because there are multiple peaks in the contaminant (for example, hydrogen sulfide) region due to the rotational structure of the atom, all of which broaden under pressure. This information can be used to determine, for example, which peaks are free of unwanted interference (e.g., from methane). This allows the processing module to take into account different operating conditions, temperature and pressure, and create and utilize a model that contains a linear regression coefficient and other variables and models that are indicative of the contaminant (e.g., hydrogen sulfide) concentration. This is significantly different than the prior art, which relies on controlled conditions and is only able to monitor a single peak under operating conditions.

In another embodiment, the first scanning source again scans from a frequency at or lower than approximately 1550 nm up through 1800 nm. However, rather than employing a second scanning source, software is used to increase the resolution through the contaminant wavelength range. In other words, the signal is processed by increasing the resolution while decreasing the bandwidth of interest. This second signal (or multiple passes thereof) is then combined with the broad waveband signal to determine the energy content and contaminant content of the fluid stream using the processing module 32 algorithms.

Using the present invention, it is possible to separate the hydrocarbon spectral signatures from the hydrogen sulfide or other contaminant spectral signatures and, therefore, to eliminate the effect of the hydrocarbon signal overlapping or interfering with the contaminant (e.g., hydrogen sulfide) signal. Once the interference from the hydrocarbons on the contaminant signal is eliminated, it is possible to detect the contaminant at low concentrations (e.g., hydrogen sulfide at concentrations as low as 1 ppm).

In any embodiment of the current invention, the absorption spectra from both the low resolution scan and the high resolution scan are stored in a database for each set of scans, along with the sample temperature and pressure. Once stored, the collected absorption signals can be standardized and analyzed through post-processing methods. For example, by taking the first derivative of the absorption spectra, the effects of contamination within the fluid infrastructure can be reduced. More specifically, by calculating the change in absorption, rather than absorption itself, it is no longer necessary to know how much spectroscopic light entered the sample, but only how much the transmitted light changed from its average value during the wavelength modulation. In addition, because the change in absorption is not dependent on source intensity, it is not necessary to use a dual beam and a second detector when scanning the fluid.

In some embodiments, the process of converting the raw spectroscopic data via the processing module 32 may then involve dividing the first derivative spectrum by the pressure (in psi) for normalization. One or more calibration models may then be applied to the normalized first derivative spectrum to calculate energy content and contaminant concentrations. It is then possible to employ multivariate empirical modeling methods to develop various calibration models. The models can use one or more of the following elements: (i) principal components analysis (PCA) and partial least squares (PLS) regression to uncover optimal modeling strategies and to detect potential outliers in the calibration data set; (ii) if any sample or spectral variables are detected in the calibration data, exclude them from being used to build the models; (iii) use of partial least squares (PLS) regression to construct predictive calibration models from the calibration data generating a series of regression coefficients which, when multiplied with the absorbance values of an unknown gas sample's spectrum, yield the property of interest; (iv) use of genetic algorithms (GA) to select subsets of the spectral response variables to use in the predictive models to make the PLS models more robust with respect to known interfering effects in the spectra; and/or (v) use of PCA to generate an "outlier model" which can be run on-line to assess whether a field-collected spectrum is abnormal with respect to the spectra that were used to develop the models.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for determining the amount of contaminants present in a fluid known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

We claim:

1. A method of determining energy content and quantity of a contaminant in a fluid comprising:
   transmitting a fluid within a fluid infrastructure through an optical cell;
   scanning said fluid over a broad wavelength range within the near infrared spectrum using a first scanning source;
   scanning said fluid over a narrow wavelength range within the near infrared spectrum using a second scanning source;
   determining energy content of said fluid using spectrographic analysis from said first scanning source scan; and
   determining a quantity of a contaminant in said fluid using spectrographic analysis from said second scanning source scan.

2. The method of claim 1 wherein said first scanning source and said second scanning source scan concurrently.

3. The method of claim 1 wherein said first scanning source and said second scanning source scan sequentially.

4. The method of claim 1 wherein said first scanning source scans at low resolution and said second scanning source scans at high resolution.

5. The method of claim 1, wherein said fluid is natural gas.

6. The method of claim 1, wherein said fluid is liquefied natural gas.

7. The method of claim 1, wherein said broad wavelength range is between about 1350 nm and about 2500 nm.

8. The method of claim 1, wherein said narrow wavelength range is between about 1560 nm and about 1610 nm.

9. The method of claim 1, wherein said contaminant is hydrogen sulfide.

10. A method of determining energy content and quantity of a contaminant in a fluid comprising:
    transmitting a fluid within a fluid infrastructure through an optical cell;
    scanning said fluid over a broad wavelength range within the near infrared spectrum using a scanning source;
    nearly simultaneously scanning said fluid over a narrow wavelength range within the near infrared spectrum using said scanning source;
    determining energy content of said fluid using spectrographic analysis from said scan of said broad wavelength range; and
    determining a quantity of a contaminant in said fluid using spectrographic analysis from said scan of said narrow wavelength range.

11. The method of claim 10 wherein said scanning source scans said broad wavelength range at low resolution and scans said narrow wavelength range at high resolution.

12. The method of claim 10, wherein said fluid is natural gas.

13. The method of claim 10, wherein said fluid is liquefied natural gas.

14. The method of claim 10, wherein said broad wavelength range is between about 1250 nm and about 2500 nm.

15. The method of claim 10, wherein said narrow wavelength range is between about 1560 nm and about 1610 nm.

16. The method of claim 10, wherein said contaminant is hydrogen sulfide.

17. A method of determining energy content and quantity of a contaminant in a fluid comprising:
    transmitting a fluid within a fluid infrastructure through an optical cell;
    scanning said fluid over a broad wavelength range within the near infrared spectrum using a scanning source;
    evaluating said broad wavelength range at low resolution to determine energy content of said fluid; and
    evaluating a narrow wavelength range within said broad wavelength range at high resolution to determine a quantity of a contaminant in said fluid.

18. The method of claim 17, wherein said fluid is natural gas.

19. The method of claim 17, wherein said fluid is liquefied natural gas.

20. The method of claim 17, wherein said broad wavelength range is between about 1250 nm and about 2500 nm.

21. The method of claim 17, wherein said narrow wavelength range is between about 1560 nm and about 1610 nm.

22. The method of claim 17, wherein said contaminant is hydrogen sulfide.

23. A system for determining energy content and quantity of a contaminant in a fluid comprising:
    an optical cell;
    a fluid infrastructure, wherein fluid in said fluid infrastructure is transmitted through said optical cell;
    a first scanning source configured to scan said fluid in said optical cell over a broad wavelength range within the near infrared spectrum;
    a second scanning source configured to scan said fluid in said optical cell over a narrow wavelength range within the near infrared spectrum, wherein energy content of said fluid is determined using spectrographic analysis from said first scanning source, and wherein quantity of contaminant is determined using spectrographic analysis from said second scanning source.

24. The method of claim 23 wherein said first scanning source and said second scanning source scan concurrently.

25. The method of claim 23 wherein said first scanning source and said second scanning source scan sequentially.

26. The method of claim 23 wherein said first scanning source scans at low resolution and said second scanning source scans at high resolution.

27. The method of claim 23, wherein said fluid is natural gas.

28. The method of claim 23, wherein said broad wavelength range is between about 1350 nm and about 2500 nm.

29. The method of claim 23, wherein said narrow wavelength range is between about 1560 nm and about 1610 nm.

30. The method of claim 23, wherein said contaminant is hydrogen sulfide.

\* \* \* \* \*